United States Patent [19]

Knollenberg

[11] Patent Number: 4,798,465

[45] Date of Patent: Jan. 17, 1989

[54] PARTICLE SIZE DETECTION DEVICE HAVING HIGH SENSITIVITY IN HIGH MOLECULAR SCATTERING ENVIRONMENT

[75] Inventor: Robert G. Knollenberg, Boulder, Colo.

[73] Assignee: Particle Measuring Systems, Inc., Boulder, Colo.

[21] Appl. No.: 851,477

[22] Filed: Apr. 14, 1986

[51] Int. Cl.[4] .................. G01N 15/02; G01N 21/00
[52] U.S. Cl. ............................. 356/336; 356/343
[58] Field of Search ........................... 356/336–343

[56] References Cited

U.S. PATENT DOCUMENTS

| | | |
|---|---|---|
| 3,941,982 | 3/1976 | Knollenberg et al. |
| 4,173,415 | 11/1979 | Wyatt ................. 356/336 |
| 4,274,745 | 6/1981 | Takahashi et al. ......... 356/427 |
| 4,429,995 | 2/1984 | Goulas ................. 356/343 |

OTHER PUBLICATIONS

"Detection and Sizing of Small Particles in an Open Cavity Gas Laser", Applied Optics, vol. 11, No. 7, Jul. 1972, pp. 1515–1520.
The Measurement of Particle Sizes Below Oil Micrometers, Robert Knollenberg, 2-85, Journal of Environmental Sciences.

*Primary Examiner*—R. A. Rosenberger
*Assistant Examiner*—Steve McGowan
*Attorney, Agent, or Firm*—Robert E. Harris

[57] ABSTRACT

A detection device is disclosed for determining particle size from particle effected light scattering in a sensing region receiving the particles in a gas carrier, such as air, and a laser beam to illuminate the sensing region. Background light from molecular scattering is reduced to a level that enables light scattered by particles having a size of at least as low as about 0.1 micron to be sensed in a high background of molecular scattering such as, for example, where molecular scattering can exceed the 0.1 micron particle's scattering by one hundred times. High molecular scattering is generated whenever the gas volume being viewed is large as is required for high flow rates, high molecular density (high pressures), or large gas molecules. This high sensitivity at high molecular scattering background is achieved through use of a linear array of detectors positioned, with respect to an imaging system, so that each detector monitors a different portion of the sensing region and provides an electrical output signal indicative of sensed particle presence within that portion monitored. The output signals from the detectors are parallel processed and coupled to a converter which provides an output indicative of the particles sensed in the entire sensing region.

20 Claims, 4 Drawing Sheets

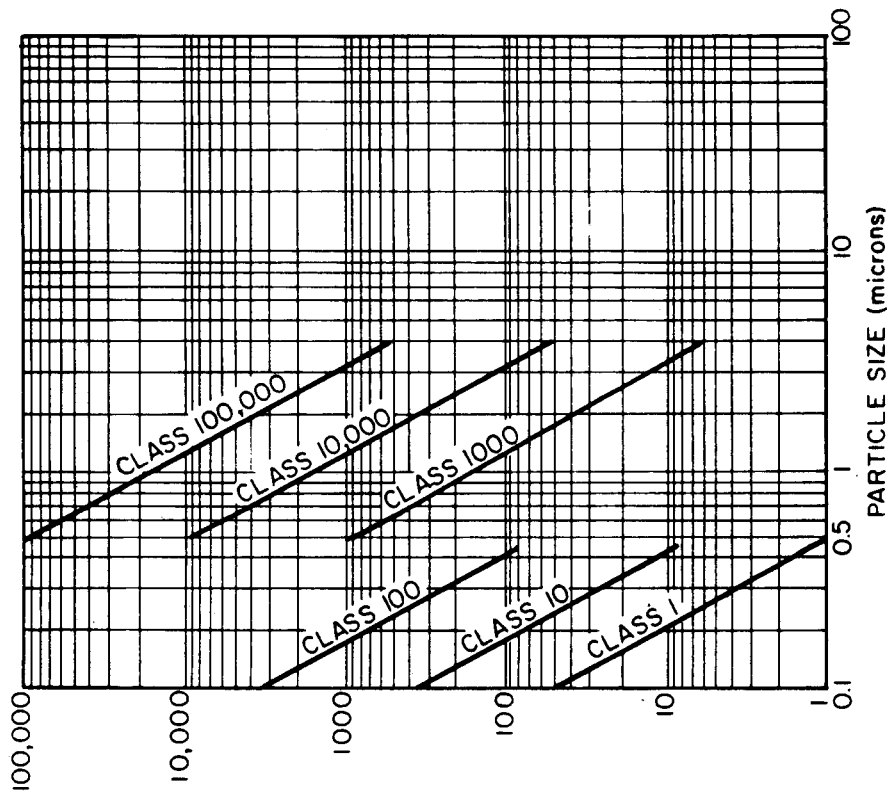
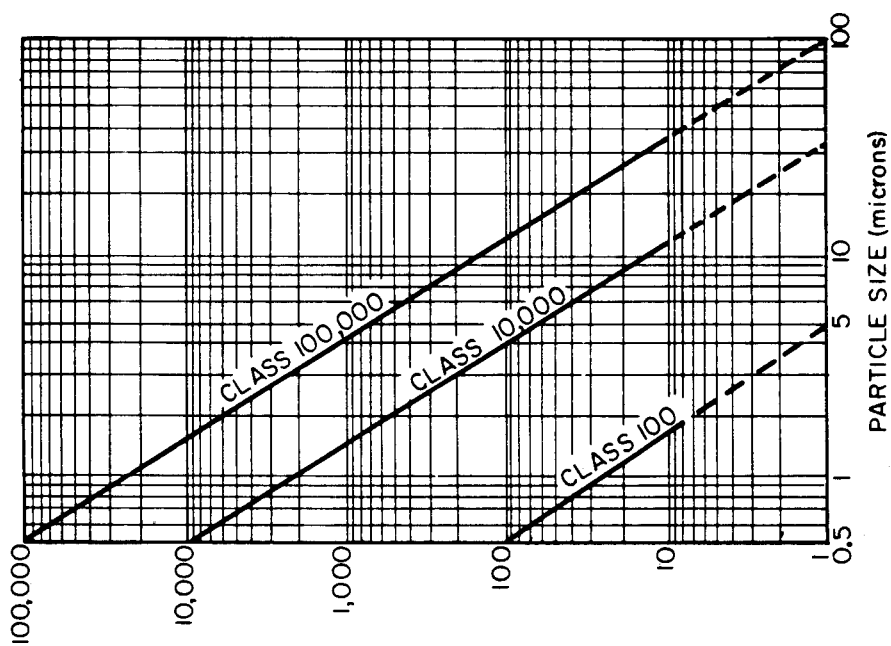

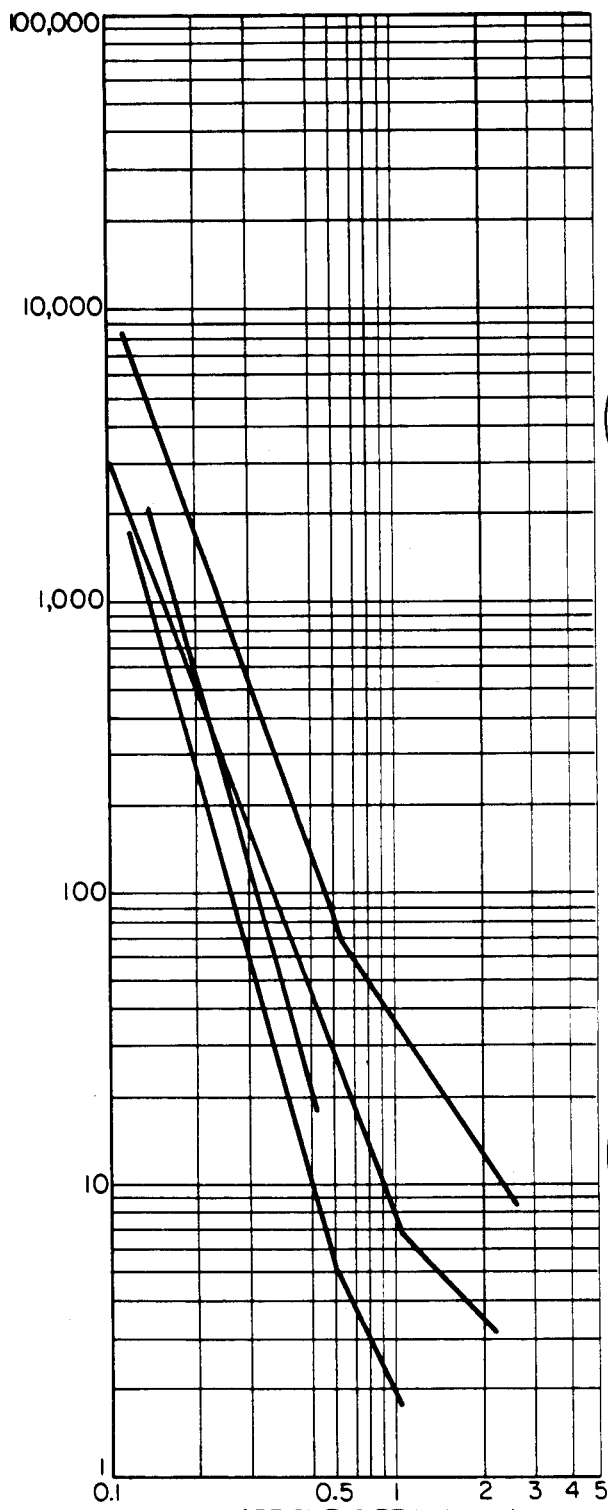
Fig_3
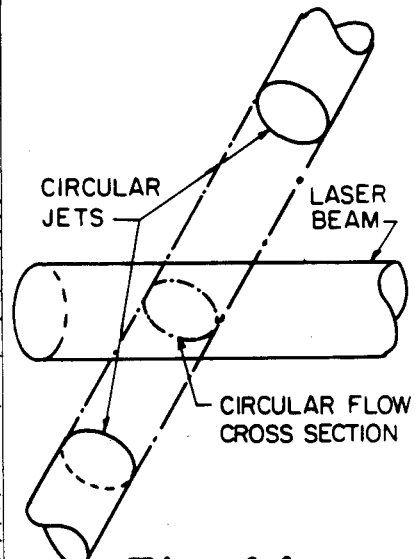
Fig_4A
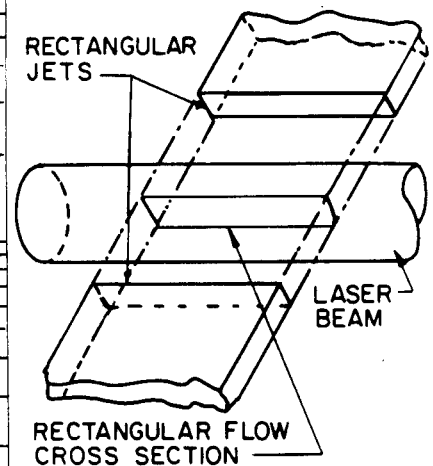
Fig_4B

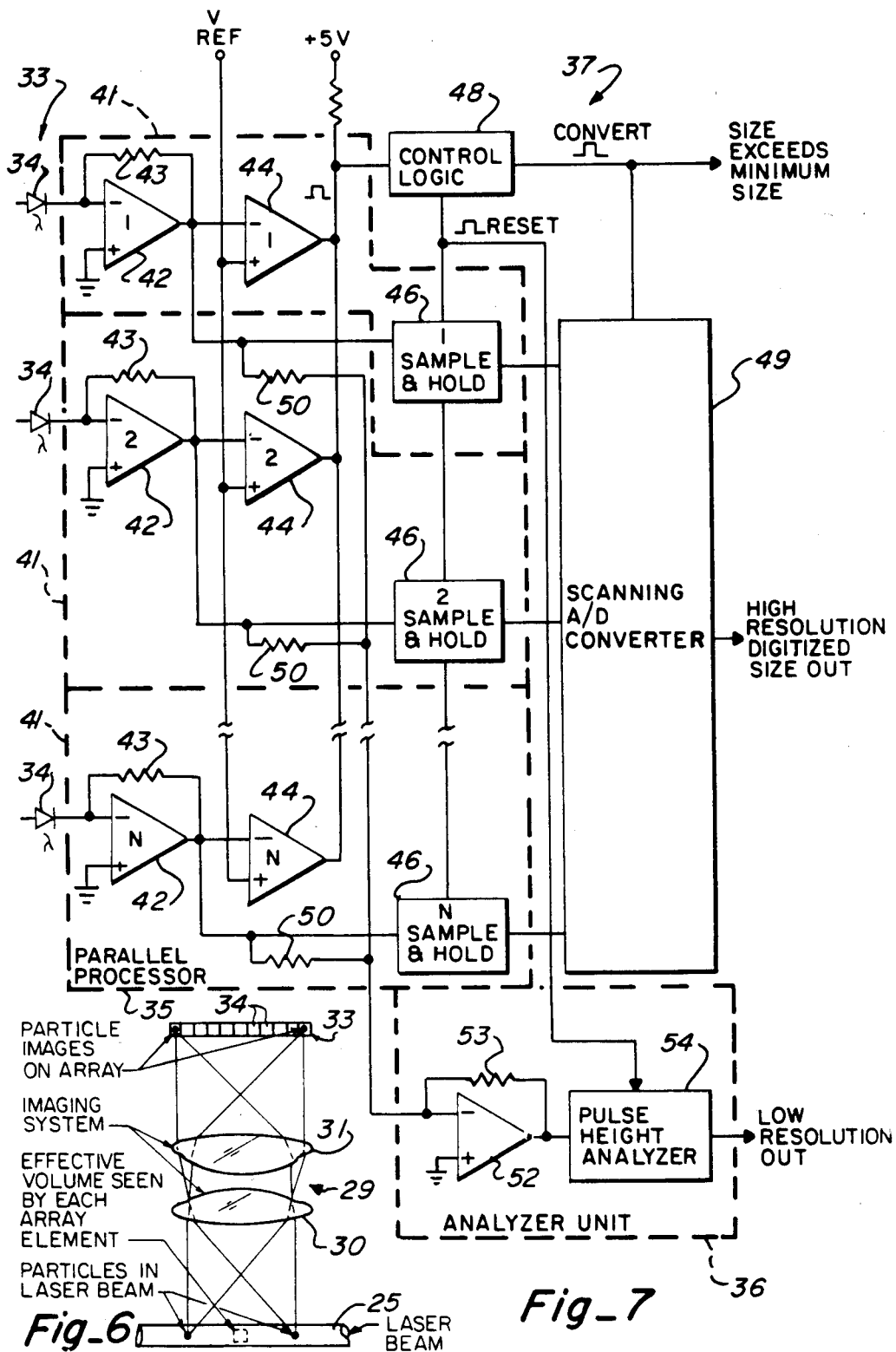
Fig_6
Fig_7

PARTICLE SIZE DETECTION DEVICE HAVING HIGH SENSITIVITY IN HIGH MOLECULAR SCATTERING ENVIRONMENT

FIELD OF THE INVENTION

This invention relates to particle size detection, and more particularly, relates to particle size detection using light scattering.

BACKGROUND OF THE INVENTION

Devices for determining particle size are now well known, and it is also well known that lasers can be, and have been, heretofore utilized to achieve particle size measurements (see, for example, U.S. Pat. No. 3,406,289 to Schleusener). In addition, particle size measurement utilizing an open cavity laser is shown and described in my U.S. Pat. No. 4,571,079, and by a passive cavity in my U.S. patent application Ser. No. 552,689, filed Nov. 17, 1983, issued June 10, 1986 as U.S. Pat. No. 4,594,715.

Refinements in extinction particle size measurement utilizing open cavity laser devices have also been heretofore described by R. G. Knollenberg and B. Schuster in "Detection and Sizing of Small Particles in Open Cavity Gas Lasers", Applied Optics, Volume 11, No. 7, November, 1972, pages 1515–1520.

Submicron particle sizing devices utilizing light scattering in an open cavity laser device has also been heretofore described by R. G. Knollenberg in "An Active Scattering Aerosol Spectrometer", Atmospheric Technology, Number 2, June, 1973, pages 80–81. Refinements have been described by R. G. Knollenberg in "Active Scattering Aerosol Spectrometry", National Bureau of Standards Special Publication 412, issued October, 1974, pages 57–64; by R. G. Knollenberg and R. E. Luehr in "Open Cavity Laser 'Active' Scattering Particle Spectrometry from 0.05 to 5 Microns", Fine Particles, Aerosol, Generation measurement, Sampling and Analysis, Editor Benjamin Y. H. Liu, Academic Press, May, 1975, pages 669–696; by R. G. Knollenberg in "Three New Instruments for Cloud Physics Measurements: The 2-D Spectrometer, the Forward Scattering Spectrometer Probe, and the Active Scattering Aerosol Spectrometer", American Meterological Society, International Conference on Cloud Physics, July, 1976, pages 554–561; by R. G. Knollenberg in "The Use of Low Power Lasers in Particle Size Spectrometry", Proceedings of the Society of Photo-Optical Instrumentation Engineers: Practical Applications of Low Power Lasers, Volume 92, August, 1976, pages 137–152; by R. G. Knollenberg in "'In Situ' Optical Particle Size Measurements in Liquid Media" presented at Semiconductor Purewater Conference, Palo Alto, Ca., Jan. 13–14, 1983; and by R. G. Knollenberg in "The Measurement of Particle Sizes Below 0.1 Micrometers", Journal of Environment Science, January-February, 1985.

A linear array of detectors has also heretofore been utilized in conjunction with parallel processing of the electrical signals generated by each detector to achieve data acquisition (see, for example, my U.S. Pat. No. 3,941,982).

Known particle measuring devices have been heretofore utilized for a variety of purposes, including determining the presence and/or size of particles in various gases, including air. With particular respect to airborne particles, tolerance limitations and the effects of particulate contamination from the environment has made it necessary to utilize effective contamination control in order to enable fabrication of many of the devices now in use. In particular, precision manufacturing, such as is required, for example, for microelectronic systems, has largely been made possible by the development and application of clean rooms and clean devices.

For many years, standard clean rooms of Class 100 or Class 1000 were more than adequate for essentially all of the electronic devices in use. However, when the present generation of micro-computers came into use, the need for micro-electronic components, such as large capacity memory chips, has resulted in the development of devices that are extremely susceptible to contamination during manufacturing.

The effects of particulate contamination during fabrication of such devices is that the yield of usable product is greatly reduced. The contamination particles can, for example, interfere with lithographic imaging integrity, or they can result in either open or short circuits, and poisoned domains, depending on their nature. At this time, microchip manufacture appears to be the most critical operation in the electronics manufacturing industry that is affected by particulate contamination.

The semiconductor VLSI (Very Large Scale Integrated Circuit) industry has continued to push the state-of-the-art in air particle counters used to certify clean rooms. The need for much higher standards reflects the demands of the VLSI circuit manufacturer as well as filtration improvements that achieve much lower levels of contamination.

Most now known aerosol counters have one cubic foot per minute (1 cfm) sample flow rates. However, to achieve reasonable statistics in a Class 1 environment, it is necessary to sample many cubic feet of air if sensitivity is limited of 0.5 microns ($\mu$m). Since the particle population increases as size decreases, most air particle counter manufacturers have therefore chosen to size much smaller particles to more readily develop the appropriate statistical base.

For example, at 0.1 $\mu$m, the average particle size distribution found in a clean room would provide nearly 100 times as many particle counts $>0.1$ $\mu$m compared to counts $>0.5$ $\mu$m. Thus, the more sensitive the particle counter the less time is required for room standard certification.

In addition, the manufacturers are producing devices with geometries including features that are smaller than 0.5 $\mu$m. Thus, in addition to generating a statistical base in the shortest period of time, higher sensitivity provides known particle size information on more potential defective generators.

With the advent of lasers, the ability to size particles via light scattering as small as 0.1 $\mu$m became a routine practice since lasers can have all of their energy focused to a small dimension of high intensity. Several devices now on the market provide 0.1 $\mu$m sensitivity but none of these devices are capable of sampling at a 1 cfm flow rate, and, in fact, are generally capable of no more than a 0.1 cfm flow rate at 0.1 $\mu$m sensitivity.

Semiconductor manufacturers also require high purity gases with low particulate microcontaminants for a variety of processes. It is necessary to make measurements at line pressures (up to 150 P.S.I.) in most cases. Some of these gases are also high molecular weight gases which scatter more light than air (i.e., a mix of largely oxygen and nitrogen) and thus molecular scattering must be reduced even if flow rates less than 1cfm are adequate.

Thus, the potential statistical advantage at smaller particle size is now partially lost in high molecular scattering environments. Clearly a combination which achieves high sensitivity in such an environment (including, for example, achieving a high flow rate of up to or exceeding 1 cfm) at high sensitivity (to detect particles having a size at least as small as 0.1 μm) is needed.

SUMMARY OF THE INVENTION

This invention provides a particle detection device having a high sensitivity in a high molecular scattering environment, with a particle size sensitivity of at least as small as 0.1 micron (0.1 μm) being achieved in such an environment. High sensitivity is achieved at high flow rates (of at least up to one cubic foot per minute), as well as in the pressure of high pressure (above atmospheric pressure) or high molecular weight gases.

This is achieved by reducing the background noise due to molecular scattering, which noise reduction is effected through use of a plurality of linear detectors, each of which senses a portion of the overall sensing region established at the intersection of the flow path of a mixture of gas and particles and a laser beam and provides an electrical output signal indicative of sensed particles with the outputs of all of the detectors being parallel processed to provide an indication of particles sensed within the entire sensing region.

It is therefore an object of this invention to provide an improved particle detection device.

It is another object of this invention to provide an improved particle detection device having high sensitivity in high molecular scattering environments.

It is another object of this invention to provide an improved particle detection device capable of providing high sensitivity including whenever the gas volume is large, the molecular density is high and/or the gas molecules are large.

It is another object of this invention to provide an improved particle detection device that reduces background noise due to molecular scattering to a level that allows detection of particle sizes at least as small as 0.1 micron in high molecular scattering environments.

It is another object of this invention to provide an improved particle detection device that allows detection of particle sizes at least as small as 0.1 micron at flow rates of up to at least one cubic foot per minute.

It is still another object of this invention to provide an improved particle detection device having a plurality of linear detectors, parallel processing of the outputs from the detectors, and a converter for providing a high resolution output signal indicative of the particles sensed in the entire sensing region monitored by the pluraity of detectors.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 illustrates a particle size distribution curve according to the classification system and size-concentration ranges as presently set forth in U.S. Federal Standard 209 (FS209);

FIG. 2 is an illustration of a particle size distribution curve according to the present planned revision of FS209;

FIG. 3 is an illustration of a particle size distribution curve showing actual count data measured in presently constructed clean rooms for the semi-conductor very large scale integrated circuit (VLSI) industry;

FIG. 4A is a partial schematic view illustrating a circular flow cross-section utilized to establish a sensing region;

FIG. 4B is a partial schematic view illustrating a rectangularly shaped flow cross-section utilized to establish a sensing region;

FIG. 6 is a simplified side sectional view illustrating positioning of the detector unit for monitoring the sensing region through an imaging system according to this invention; and FIG. 7 is a simplified electronic schematic and block diagram illustrating electronic signal processing according to this invention.

DESCRIPTION OF THE INVENTION

Figure 5:
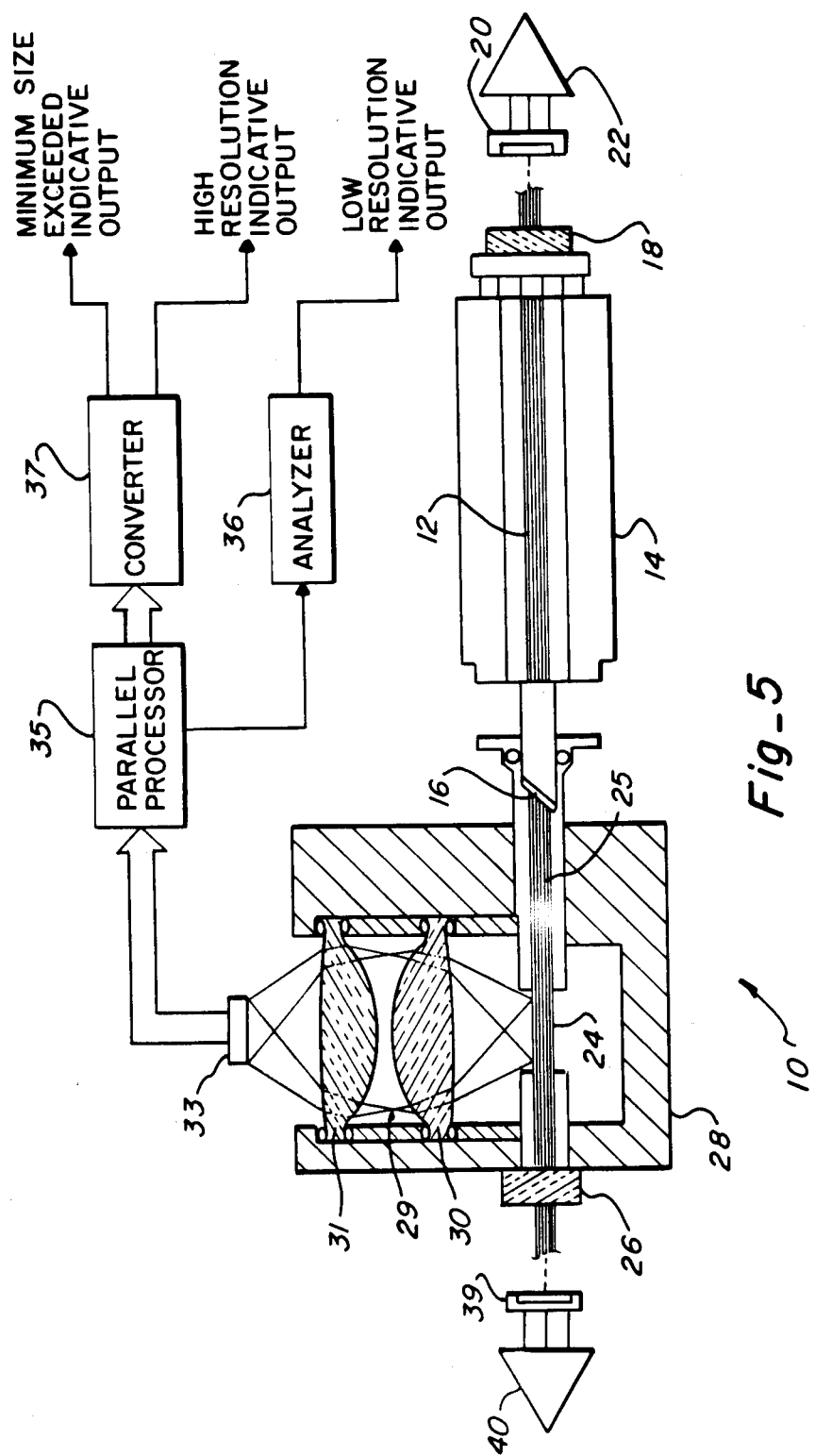
FIG. 5 is a simplified side section view schematic presentation of a particle size measuring device having an open cavity laser and having this invention utilized in conjunction therewith.

Present-day particle control in electronic manufacturing areas is based mainly on application of U.S. Federal Standard 209 (FS209), the German VDI 2083 document, or similar standards. FIG. 1 shows the present classification system and the size-concentration ranges used in FS209. Total particles/cubic foot are shown in the left vertical column of FIG. 1 (and also in FIGS. 2 and 3), and, as shown, are equal to and larger than the stated particle size. Counts below 10 (0.35) particles per cubic foot (liter) are unreliable (and hence shown in dotted lines) except when a large number of samplings is taken. As can be seen, the smallest particle that needs to be measured is 0.5 micron in diameter, and the maximum cleanliness level specified is 100 particles per cubic foot.

These clean room standards, however, have been in existence for several years, and present requirements for electronic products have shown that the level covered is not satisfactory for reasonable production of microelectronic devices since particle control requirements have now become more restrictive. The need for revised particle contamination level definitions has therefore become apparent, and, for that reason, plans are under way to modify FS209 to allow measurements to be made including smaller particles and cleaner levels.

While a revision of FS209 is now underway under the direction of the Institute of Environmental Science, this revision is not yet complete. One of the major objectives of the revision is to define a room, or area, air cleanliness class at the Class 10 level, and to permit measurement of particles in sizes below 0.5 micron in diameter so as to allow adequate statistical definitions at the lower levels. It can be expected that the standard used in all industrial areas will also probably soon be revised, and revision of FS209 therefore appears to be only the first in a series of new standards. In fact, Class 1 levels are currently capable of being produced, and must also be addressed in the near future.

Since particle concentration increases rapidly as particle size decreases, the advisability of measurements of smaller particles appears reasonable. Therefore, plans for the revised FS209 involve measurements at 0.3 μm, and at 0.1 μm for cleaner areas. FIG. 2 shows the presently planned format of the classifications, allowing measurement at sizes below 0.5 μm. However, it should be noted that the slopes of the classification curves in FIG. 2 are based on the same slopes as in the present FS209.

Consideration is being given to modification of the slopes of the classification curves in accordance with more recent data that have been obtained in a few VLSI clean rooms in the United States. A laser counter was used to measure from 0.1 μm up, and the data obtained are shown in FIG. 3. It appears that the particle size distribution in very clean rooms has a much steeper slope below the 1.0 μm size than would be expected from the present FS209 classification curves, and there is some possibility of making the slopes steeper as shown in FIG. 3.

If the classification curves are extended to the 0.1 μm size range, then the time and effort to obtain valid data for rooms of Class 100 and better will be reduced regardless of whether FS209 is simply extrapolated or revised according to the more recent data of FIG. 3.

Development of a device that can achieve a sensitivity of 0.1 micron in a high molecular scattering environment, as has been accomplished in this invention, was not readily achieved. With respect to a molecular scattering environment due to high flow rates of up to, or exceeding one cubic foot per minute, such rates dictate a fairly large cross section of flow passing through the sensitive volume of an optical sensing device.

Even at sonic velocities, the cross-section is 1.8 mm², and full sonic flow is impossible to achieve by practical vacuum sources. Thus, the more typical flow velocities are ⅓ to ½ sonic, and the flow cross sections increase to 4-5 mm² in typical instruments at 1 cfm. This large cross-section of flow must be illuminated uniformly if particles are to be sized accurately.

Thus, the illuminated region cannot be near a small focused region of a laser but must ordinarily be placed in an expanded laser beam, if the flow cross section is circular as indicated in FIG. 4(a), or stretched along the beam axis, if the flow cross section is made rectangular as illustrated in FIG. 4(b). Thus, a near optimum design, as utilized in this invention, has a flow cross section of $1 \times 10$ mm² and collecting optics as shown similar to that shown in my in U.S. Pat. No. 4,571,079 and in my U.S. patent application Ser. No. 552,689, filed Nov. 17, 1983.

The laser itself must generate about 1 watt of power within the sensing region in order to produce 0.1 μm sensitivity. A reasonant HeNe laser cavity operating at 633 nm is the most expedient method of generating the required power, although any 1 watt visible light laser can be used (e.g., argon ion). Thus, since light sources can be devised to provide the energy density sufficient to sense particles as small as 0.1 μm and enable cross-sections permitting 1 cfm, the problem would appear to be straightforward.

This would have been the case if the particles were the only source of light scattering within the sensing region. By careful design, stray light can be effectively eliminated. However, there are approximately $10^{16}$ air molecules per cubic mm accompanying the airborne particles as they transit the laser beam and these air molecules cannot be eliminated. Calculatins show that such a volume of air scatters over 100 times more energy than a typical 0.1 μm particle (see "The Measurement of Particle Sizes Below 0.1 Micrometers" by R. G. Knollenberg appearing the The Journal of Environmental Sciences, January-February, 1985). Since the large ensemble of molecular scatters is ever present, this signal source is largely d.c.

It is the variations (a.c.) in the molecular scattering signal (a.c. noise) that mask the desired 0.1 μm particle signal. This noise is itself proportional to the d.c. molecular scattering signal. If the noise source is classical Shott noise, it is proportional to the square root of the d.c. signal. However, with laser sources, the noise is higher than calculated by the Shott noise assumption, and laser cavities are easily randomly modulated (generating noise) by the flow itself. In such cases, the a.c. noise is directly proportional to the d.c. component instead of the square root. Measurements reveal that in most 1cfm systems the molecular scattering noise is 5 to 10 times that of a 0.1 μm particle, marking detection impossible with known devices.

A high molecular scattering environment, or background, exists, for example, when molecular scattering can exceed the 0.1 micron particles scattered by one hundred times. Such high molecular scattering can be generated, not only when the gas volume being viewed is large as is required for high flow rates, but also can be generated, for example, due to high molecular density (high pressures above ambient) or due to the presence of large gas molecules. In any case, whenever a high molecular scattering background in encountered, the device of this invention can be utilized to enable high sensitivity to be achieved in the presence of the high molecular scattering background.

In this invention, an illumination system is utilized to illuminate a sensing region, or volume, through which a gas (usually air), having the particles to be sensed therein, is caused to flow. The illumination system is preferably, as indicated in FIG. 5, a laser beam illumination system 10, such as is shown in my U.S. Pat. No. 4,571,079 and my U.S. patent application Ser. No. 552,689, filed Nov. 17, 1983.

As shown in FIG. 5, access to laser cavity 12 can be gained by terminating plasma tube 14 at one end with a Brewster's window 16. A curved mirror 18 (with radius r=100 cm, for example) is positioned at the other end of tube 14. A photodetector 20 and preamplifier 22 are conventionally positioned along the laser beam axis outside mirror 18 to provide a measure of relative intensity of illumination.

For particle size measurement, particles to be size measured are injected through jets 24 so that the particles pass through laser beam 25 between the Brewster's window 16 and an external laser mirror 26 (with r=70 cm, for example).

As shown in FIG. 2, optical sampling block 28 is positioned adjacent to the particle injection area, and block 28 positions light collecting optical elements, or imaging system, 29, which system may include, as shown, a pair of lenses 30 and 31, above and close to the particle injection area.

A photodetector unit 33, having a plurality of detectors 34 (as indicated in FIGS. 6 and 7), is positioned adjacent to block 28, so that photodetector unit 33 is located in the focal plane of lenses 30 and 31. The electrical signal outputs from photodetector unit 33 is coupled to parallel processor 35. The output of parallel processor 35 may be coupled through analyzer unit 36 to provide a low resolution indicative output, and is coupled through converter unit 37 to provide a digital particle size high resolution indicative output. In addition, a minimum size exceeded indicative output is also provided from converter unit 37.

Photodetector 39 and preamplifier 40 may be optionally positioned along the laser beam axis at the other side of mirror 26 to provide a reference measurement, as does photodetector 20 and preamplifier 22.

In this invention, noise is reduced by using an imaging system and detector array to reduce the background light from molecular scattering to manageable levels. As shown best in FIG. 6, detector unit 33 includes a linear array of rectangular elements, or detectors, 34 (eleven of which are indicated in FIG. 6 for illustration purposes). The use of a linear array of detectors connected to parallel processing circuitry for two-dimenional data acquisition is described in my U.S. Pat. No. 3,941,982.

This array of elements (which may be photodiodes as indicated in FIG. 7) view corresponding volumes (i.e., a portion of the entire sensing region) within the laser beam. Light scattered from a particle is reimaged onto a single element as a bright image along with a background of diffuse molecular scattering produced by all of the air molecules in a particular element's monitored portion of the overall sensing region.

Thus, the amount of background molecular scattering is reduced by the number of elements selected for the array. For light noise sources other than those described by Shott noise, there is also a direct reduction in noise proportional to the number of array elements. For Shott noise sources, the noise reduction is proportional to the square root of the number of array elements.

Since there are N independent detectors utilized in this invention, the electrical signal output from each must be individually interrogated to determine when a particle image has been observed by any one element. FIG. 7 illustrates a plurality of detectors 34 forming detection unit 33, with each detector being connected to a different signal processing circuit 41 of parallel processor 35. More particularly, each detector 34 is connected with preamplifier 42 (each of which amplifiers has a feedback resistor 43 connected between the output and the negative input) in each signal processing circuit 41. Each processing circuit 41 also includes a comparator 44 and a peak storage element (sample and hold circuit) 46.

Each preamplifier 42 develops an amplified electrical signal of the noise and particle event, which signal is coupled to the comparator 44 associated therewith. The threshold level of the comparator is set at the signal peak amplitude of the minimum detectable particle size. The comparator outputs are OR'ed together through control logic unit 48 which provides a particle transit time pulse for timing purposes and an indication of when a particle of minimum detectable size has been detected.

For sizes larger than the minimum detectable size, resolving the size depends upon the amount of resolution desired. If a simple count of all particles >0.1 μm in a single size channel is desired, for example, signal processing circuits 41 may simply be utilized in combination with control logic unit 48.

For high resolution multi-channel applications (e.g., where 0.01 μm resolution is desired with 10 channels between 0.1 μm and 0.2 μm), it is necessary to individually store the peak amplitudes of each detector prior to processing. For such high resolution (e.g., where the second threshold is at 0.11 μm), the output from each preamplifier 42 is coupled to its associated peak storing unit (sample and hold circuit) 46 which stores the peak amplitude. The peak amplitudes stored in sample and hold circuits 46 are then individually read out by converter unit 37, which includes control logic unit 48 and scanning A/D converter 49 (as indicated in FIG. 7).

For low resolution multi-channel applications, it is sufficient to sum all of the outputs from amplifiers 42 by coupling each output through an associated resistor 50 to summing amplifier 52 (which has a feedback resistor 53 connected between the output and the negative input) of analyzer unit 36, which unit also includes a conventional pulse height analyzer 54 to receive the outputs from amplifier 52. Such a low resolution application implies that the second threshold level to be used is sufficiently higher than the first such that the summed noise is still smaller than peak amplitudes which exceed the second threshold level. For example, if the second threshold is 0.2 μm, it would be about 40× greater than the 0.1 μm threshold, and the summed noise would be much less than such a high threshold.

Each signal processing circuit, in conjunction with its associated detector, thus determines when a particle event has occurred and the magnitude of the scattering event, which can be shared between two elements when the image is at the boundary or slightly out of focus.

In operation, a laser beam is directed through the sensing region and a gas having particles therein is caused to flow through the sensing region at flow rates that can include a flow of at least about 1 cfm. Particles within the sensing region cause light scattering, with such light scattering due to particles having a diameter down to at least 0.1 μm and larger being detectable by the array of detectors. Each detector of the array of detectors monitors a predetermined volume of the sensing region, senses detectable light scattering within the monitored portion, and provides an electrical output signal indicative of sensed light scattering (along with signals caused by background noise). The electrical output signals are parallel processed and the peak amplitudes stored for high resolution (or alternately summed and analyzed for low resolution). To achieve high resolution readout, the stored peak amplitudes are thereafter individually read out and converted to a digital output.

In a working embodiment of this invention, a particle size sensitivity of 0.1 micron has been achieved in a high molecular scattering environment represented by a flow rate of 1 cubic foot per minute.

This invention thus provides an improved particle size detection device that is capable of achieving high sensitivity in a high molecular scattering environment through use of an array of detectors to provide needed noise reduction due to the molecular scattering background.

What is claimed is:

1. A particle size detection device capable of operation with high sensitivity in a high molecular scattering environment, said device comprising:
   first means for enabling a mixture of gas and particles to be passed through a predetermined sensing region such that a high molecular scattering background is present at said sensing region;
   second means for illuminating said sensing region so that particles in said sensing region cause light scattering; and detecting and processing means for receiving light scattered at said sensing region, said detecting and processing means being configured to reduce noise due to background light from molecular scattering occurring within said sensing region to a level that enables detection and processing of light scattered by particles within said sensing region having a diameter of at least as small as 0.1 micron and larger, said detecting and processing means providing an electrical signal output indicative of the presence of such particles sensed in said sensing region.

2. The device of claim 1 wherein said device includes means for causing at least one of high flow rate, high pressure and large gas molecules so that said high molecular scattering background is due to at least one of high flow rate, high pressure, and large gas molecules.

3. The device of claim 1 wherein said first means has a size sufficient to enable flow of said mixture of gas and particles therethrough at a rate of at least about 1 cubic foot per minute.

4. The device of claim 1 wherein said first means includes one of a substantially circular and a substantially rectangularly shaped conduit adjacent to said sensing region.

5. The device of claim 1 wherein said second means includes laser means for directing a laser beam through said sensing region to provide said illumination thereat.

6. The device of claim 1 wherein said detecting and processing means includes a plurality of detectors each of which monitors a different predetermined portion of said sensing region.

7. The device of claim 6 wherein said plurality of detectors includes a linear array of detectors, wherein said detecting and processing means includes imaging means positioned between said detectors and said sensing region, and wherein each of said linear array of detectors is substantially rectangularly shaped and detects, through said imaging means, a substantially rectangular volume as said predetermined portion of said sensing region.

8. The device of claim 6 wherein said detecting and processing means is a parallel processor that includes a plurality of processing circuits each of which is connected with a different one of said plurality of detectors to separately process the electrical signal outputs therefrom.

9. The device of claim 8 wherein each of said processing circuits includes amplifier means and peak storing means connected to receive the output from said amplifier means, and wherein said detecting and processing means also includes converting means connected with each of said peak storing means for receiving the outputs therefrom and responsive thereto providing said output indicative of particles sensed within said entire sensing region.

10. The device of claim 9 wherein each of said processing circuits includes comparator means connected to receive the output from said amplifier means, and wherein said converting means includes a scanning analog-to-digital converter connected to receive the outputs from said peak storage means and control logic means connected to receive the outputs from said comparator means, said control logic means being also connected with said peak storage means and said scanning analog-to-digital converter to control coupling of said outputs from said peak storage means to said converter.

11. The device of claim 8 wherein said detecting and processing means includes summing means and analyzer means for providing an indication of particles sensed within said sensing region having predetermined particle diameters larger than 0.1 micron.

12. In a particle size detecting device having first means for enabling a mixture of gas and solid particles to be passed through a predetermined sensing region in a manner such that a high molecular scattering background is present at said sensing region, and second means for causing an illuminating beam to be passed through said sensing region such that particles within said sensing region cause light scattering, an improved particle sensing system comprising:

detection means for receiving and detecting light scattered by said particles in said mixture passed through said sensing region, said detection means including an array of detectors each of which monitors a predetermined different cubic portion of said sensing region whereby substantially said entire sensing region is monitored by said detection means, with each of said array of detectors providing an electrical signal output indicative of sensed particles having a diameter at least as small as 0.1 micron and larger in said portion of said sensing region monitored by that detector;

a plurality of signal processing means each of which is connected with a different one of said array of detectors to separately receive the electrical signal output therefrom, with each of said signal processing means providing an output indicative of sensed particles at least as small as 0.1 micron and larger; and combining means connected with each of said signal processing means to receive the outputs therefrom and responsive thereto providing an output indicative of at least a portion of said sensed particles within said entire sensing region.

13. The system of claim 12 wherein each of said plurality of signal processing means includes amplifying means and peak storing means connected to receive the output from said amplifying means.

14. The detector of claim 13 wherein each of said peak storing means is a sample and hold circuit, wherein said combining means includes a scanning analog-to-digital converter connected to receive the outputs from said sample and hold circuits and control logic means connected to receive the outputs from said comparators, said control logic means also being connected with said scanning analog-to-digital converter and said sample and hold circuits to provide timing signals thereto.

15. The device of claim 12 wherein said combining means includes a summing amplifier and a pulse height analyzer for providing an output of sensed particles having predetermined particle diameters larger than 0.1 micron.

16. The device of claim 12 wherein said first means enables a flow rate therethrough of at least about 1 cubic foot per minute, and wherein said detection means is able to provide a scattered particle size sensitivity of about 0.1 micron at a flow rate of about 1 cubic foot per minute.

17. A particle size detection device capable of operating with high sensitivity at high flow rates, said device comprising:

conduit means providing a flow path for a mixture of particles and gas through a predetermined sensing region with the capacity of flow of said mixture through said sensing region including a rate of at least about one cubic foot per minute;

laser means providing a laser beam passing through said sensing region;

imaging means positioned adjacent to said sensing region;

a linear array of detectors each of which is adapted to monitor a different portion of said sensing region through said imaging means and sense light scattered at said sensing region by particles within said portion of said sensing region, with each of said detectors sensing particles having a diameter of about 0.1 micron and larger and providing an electrical signal output indicative thereof;

a plurality of signal processing circuits each of which includes an amplifier connected with a different one of said detectors of said linear array of detectors, a comparator connected with said amplifier and receiving a predetermined threshold reference voltage, and a sample and hold circuit connected with said amplifier;

a control logic unit connected with said comparators to commonly receive the outputs therefrom and provide a particle transit time pulse output; and a scanning analog-to-digital converter connected with said control logic circuit to receive said particle transit time pulse output therefrom, and connected with said sample and hold circuits to sequentially receive said outputs therefrom and provide a high resolution digital output signal indicative of particles sensed within said entire sensing region.

18. The device of claim 17 wherein each of said detectors is substantially rectangularly shaped, and wherein said imaging means causes each said portion of said sensing region monitored by said detectors to be a substantially cubic volume such that said entire sensing region is collectively monitored by said array of detectors.

19. The device of claim 17 wherein said device includes output means connected with said comparators through said control logic unit to provide an output indicating sensing of particles exceeding a predetermined minimum size.

20. The device of claim 17 wherein said device includes summing amplifier means connected to receive the outputs from said amplifiers of said plurality of signal processing circuits and pulse height analyzer means connected with said summing amplifier whereby said device is capable of providing an output having a resolution less than that of said output provided by said scanning analog-to-digital converter.

* * * * *

REEXAMINATION CERTIFICATE (1559th)
United States Patent [19]
Knollenberg

[11] B1 4,798,465
[45] Certificate Issued Sep. 17, 1991

[54] PARTICLE SIZE DETECTION DEVICE HAVING HIGH SENSITIVITY IN HIGH MOLECULAR SCATTERING ENVIRONMENT

[75] Inventor: Robert G. Knollenberg, Boulder, Colo.

[73] Assignee: Particle Measuring Systems, Inc.

Reexamination Request:
No. 90/002,102, Aug. 6, 1990

Reexamination Certificate for:
Patent No.: 4,798,465
Issued: Jan. 17, 1989
Appl. No.: 851,477
Filed: Apr. 14, 1986

[51] Int. Cl.$^5$ .................. G01N 15/02; G01N 21/00
[52] U.S. Cl. ............................. 356/336; 356/343
[58] Field of Search .............. 356/336, 337, 338, 339, 356/343

[56] References Cited
U.S. PATENT DOCUMENTS

| | | | |
|---|---|---|---|
| 3,770,351 | 11/1973 | Wyatt | 356/336 |
| 3,941,982 | 3/1976 | Knollenberg et al. | 377/54 |
| 4,075,462 | 2/1978 | Rowe | 377/10 |
| 4,243,318 | 1/1981 | Stöhr | 356/39 |
| 4,318,140 | 3/1982 | Lundqvist et al. | 356/442 |
| 4,348,111 | 9/1982 | Goulas et al. | 356/336 |
| 4,693,602 | 9/1987 | Wyatt et al. | 356/336 |

OTHER PUBLICATIONS

Faxvog, "New Laser Particle Sizing Instrument", Rsearch Publication GMR-2263, Research Laboratories, General Motors Corporation, Warren, Mich., Oct. 1976.

Primary Examiner—R. A. Rosenberger

[57] ABSTRACT

A detection device is disclosed for determining particle size from particle effected light scattering in a sensing region receiving the particles in a gas carrier, such as air, and a laser beam to illuminate the sensing region. Background light from molecular scattering is reduced to a level that enables light scattered by particles having a size of at least as low as about 0.1 micron to be sensed in a high background of molecular scattering such as, for example, where molecular scattering can exceed the 0.1 micron particle's scattering by one hundred times. High molecular scattering is generated whenever the gas volume being viewed is large as is required for high flow rates, high molecular density (high pressures), or large gas molecules. This high sensitivity at high molecular scattering background is achieved through use of a linear array of detectors positioned, with respect to an imaging system, so that each detector monitors a different portion of the sensing region and provides an electrical output signal indicative of sensed particle pressure within that portion monitored. The output signals from the detectors are parallel processed and coupled to a converter which provides an output indicative of the particles sensed in the entire sensing region.

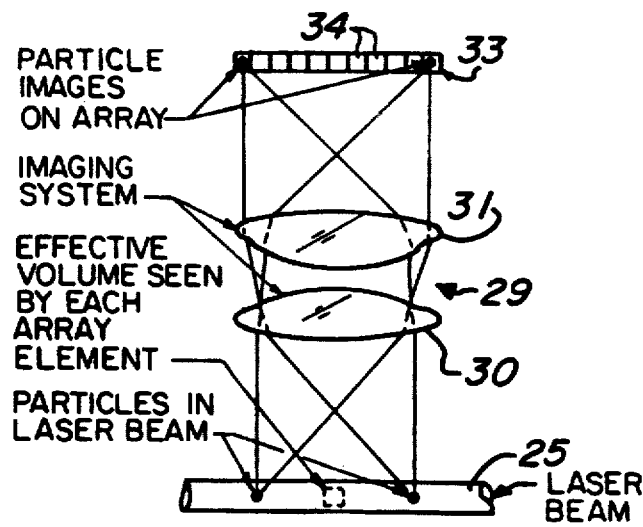

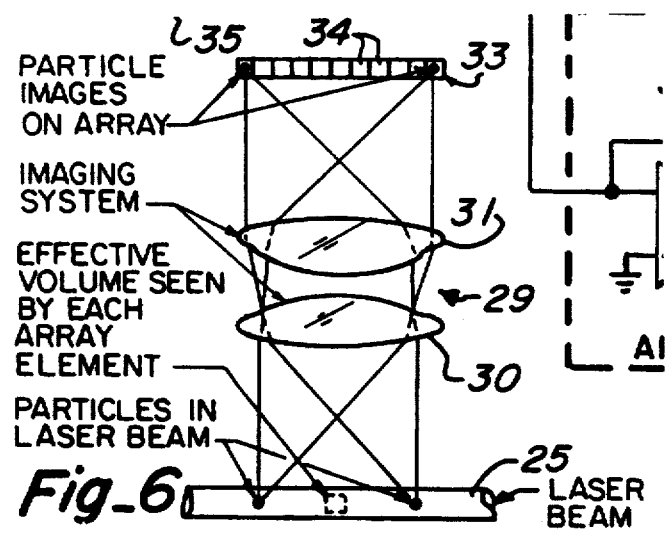
Fig_6

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 12-20 is confirmed.

Claims 1, 3, 6 are determined to be patentable as amended.

Claims 2-5, 7-11, dependent on an amended claim, are determined to be patentable.

1. A particle size detection device capable of operation with high sensitivity in a high molecular scattering environment, said device comprising:
   first means for enabling a mixture of gas and particles to be passed through a predetermined sensing region such that a high molecular scattering background is present at said sensing region *that includes noise due to background light from molecular scattering exceeding light scattered by particles to be detected at said sensing region;*
   second means for illuminating said sensing region so that particles in said sensing region cause light scattering; and
   detecting and processing means for receiving light scattered at said sensing region, said detecting and processing means being configured to reduce *said* noise due to background light from molecular scattering occurring within said sensing region to a level that enables detection and processing of light scattered by particles within said sensing region having a diameter of at least as small as 0.1 micron and larger, said detecting and processing means providing an electrical signal output indicative of the presence of such particles sensed in said sensing region.

3. [The] *A particle size detection* device [of claim 1 wherein said] *capable of operation with high sensitivity in a high molecular scattering environment, said device comprising:*
   first means [has] *for enabling a mixture of gas and particles to be passed through a predetermined sensing region such that a high molecular scattering background is present at said sensing region, said first means having* a size sufficient to enable flow of said mixture of gas and particles therethrough at a rate of at least about 1 cubic foot per minute;
   second means for illuminating said sensing region so that particles in said sensing region cause light scattering; and
   detecting and processing means for receiving light scattered at said sensing region, said detecting and processing means being configured to reduce noise due to background light from molecular scattering occurring within said sensing region to a level that enables detection and processing of light scattered by particles within said sensing region having a diameter of at least as small as 0.1 micron and larger, said detecting and processing means providing an electrical signal output indicative of the presence of such particles sensed in said sensing region.

6. [The] *A particle size detection* device [of claim 1 wherein] *capable of operation with high sensitivity in a high molecular scattering environment, said device comprising:*
   *first means for enabling a mixture of gas and particles to be passed through a predetermined sensing region such that a high molecular scattering background is present at said sensing region;*
   *second means for illuminating said sensing region so that particles in said sensing region cause light scattering; and*
   *detecting and processing means for receiving light scattered at said sensing region, said detecting and processing means being configured to reduce noise due to background light from molecular scattering occurring within said sensing region to a level that enables detection and processing of light scattered by particles within said sensing region having a diameter of at least as small as 0.1 micron and larger,* said detecting and processing means [includes] *including* a plurality of detectors each of which monitors a different predetermined portion of said sensing region, *and said detecting and processing means providing an electrical signal output indicative of the presence of such particles sensed in said sensing region.*

* * * * *

REEXAMINATION CERTIFICATE (2365th)

United States Patent [19]

Knollenberg

[11] B1 4,798,465

[45] Certificate Issued Aug. 30, 1994

[54] PARTICLE SIZE DETECTION DEVICE HAVING HIGH SENSITIVITY IN HIGH MOLECULAR SCATTERING ENVIRONMENT

[75] Inventor: Robert G. Knollenberg, Boulder, Colo.

[73] Assignee: Particle Measuring Systems, Inc., Boulder, Colo.

Reexamination Request:
No. 90/003,299, Jan. 7, 1994

Reexamination Certificate for:
Patent No.: 4,798,465
Issued: Jan. 17, 1989
Appl. No.: 851,477
Filed: Apr. 14, 1986

[51] Int. Cl.$^5$ .................. G01N 15/02; G01N 21/00
[52] U.S. Cl. ................................ 356/336; 356/343
[58] Field of Search ........................... 356/336, 343

[56] References Cited

U.S. PATENT DOCUMENTS 3,705,771 12/1972 Friedman et al.
4,273,443 6/1981 Hogs.

OTHER PUBLICATIONS

Borso, Charles S.; "Oqtimization of Monolithic Solid State Array Detectors for the Position Encoding of Small Angle X-ray Scattering From Synchrotron Sources", Nuclear Instruments and Methods, Vol. 204, Pages 65-72 (1982).

*Primary Examiner*—R. A. Rosenberger

[57] ABSTRACT

A detection device is disclosed for determining particle size from particle effected light scattering in a sensing region receiving the particles in a gas carrier, such as air, and a laser beam to illuminate the sensing region. Background light from molecular scattering is reduced to a level that enables light scattered by particles having a size of at least as low as about 0.1 micron to be sensed in a high background of molecular scattering such as, for example, where molecular scattering can exceed the 0.1 micron particle's scattering by one hundred times. High molecular scattering is generated whenever the gas volume being viewed is large as is required for high flow rates, high molecular density (high pressures), or large gas molecules. This high sensitivity at high molecular scattering background is achieved through use of a linear array of detectors positioned, with respect to an imaging system, so that each detector monitors a different portion of the sensing region and provides an electrical output signal indicative of sensed particle presence within that portion monitored. The output signals from the detectors are parallel processed and coupled to a converter which provides an output indicative of the particles sensed in the entire sensing region.

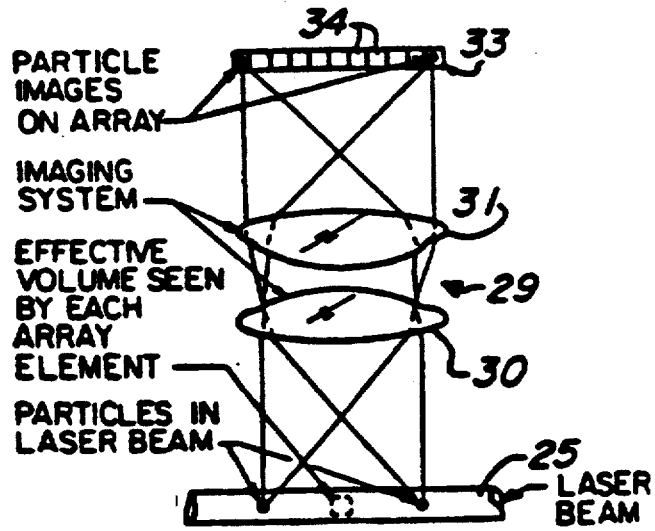

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-20 is confirmed.

* * * * *